United States Patent [19]

Nomoto et al.

[11] 4,352,801
[45] Oct. 5, 1982

[54] CEPHEM DERIVATIVES AND ANTIBACTERIAL AGENTS COMPRISING SAID COMPOUNDS

[75] Inventors: Seiichiro Nomoto; Hironori Ikuta, both of Tokyo; Yoshimasa Machida, Wako; Shigeto Negi, Kodaira; Isao Sugiyama, Tokyo; Hiroshi Yamauchi, Gifu; Kenro Nakatsuka, Matsudo; Isao Saito, Sakura, all of Japan

[73] Assignee: Eisai Co., Ltd., Tokyo, Japan

[21] Appl. No.: 218,402

[22] Filed: Dec. 19, 1980

[30] Foreign Application Priority Data

Oct. 7, 1980 [JP] Japan ................................. 55-139269

[51] Int. Cl.³ .......................................... C07D 501/36
[52] U.S. Cl. ...................................... 424/246; 544/27; 544/22; 544/28
[58] Field of Search ....................... 544/27, 28, 21, 22; 424/246

[56] References Cited

U.S. PATENT DOCUMENTS 4,285,941 8/1981 Machida et al. ...................... 544/27

Primary Examiner—Nicholas S. Rizzo
Attorney, Agent, or Firm—Wenderoth, Lind & Ponack

[57] ABSTRACT

Cephem derivatives represented by the formula:

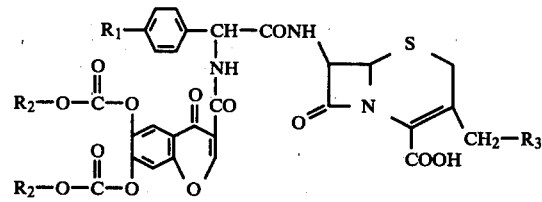

wherein $R_1$ represents a hydrogen atom or a hydroxyl group, $R_2$ represents a lower alkyl group or a chloro-substituted lower alkyl group, and $R_3$ represents a lower alkanoyloxy group or a nitrogen-containing heterocyclic thio group, and the pharmaceutically acceptable salts thereof. The cephem derivatives exhibit excellent antibacterial activity and are effective against Gram-positive and Gram-negative bacteria.

5 Claims, No Drawings

CEPHEM DERIVATIVES AND ANTIBACTERIAL AGENTS COMPRISING SAID COMPOUNDS

This invention relates to novel cephem derivatives represented by the formula:

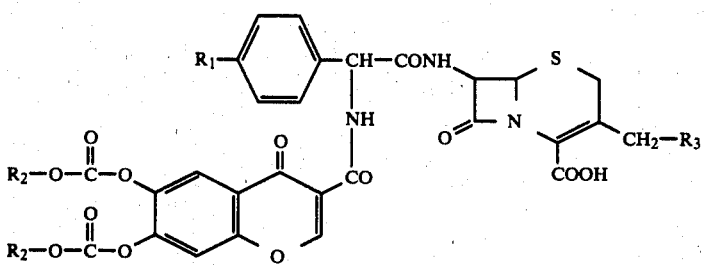

wherein $R_1$ represents a hydrogen atom or a hydroxyl group, $R_2$ represents a lower alkyl group or a chloro-substituted lower alkyl group, and $R_3$ represents a lower alkanoyloxy group or a nitrogen-containing heterocyclic thio group,
the pharmaceutically acceptable salts thereof, a process for production thereof, and antibacterial agents comprising them.

Examples of the lower alkyl group for $R_2$ in the formula (I) are methyl, ethyl, propyl, butyl and the like, and the chloro-substituted lower alkyl group includes groups resulting from substitution of a chlorine atom for one or more hydrogen atoms of a lower alkyl group, for example, 2,2,2-trichloroethyl and the like.

The lower alkanoyloxy group for $R_3$ represents acetoxy, propionyloxy and the like.

The nitrogen-containing heterocyclic thio group for $R_3$ denotes heterocyclic thio groups containing at least one nitrogen atom as a hetero atom and substitution products thereof. The nitrogen-containing heterocyclic groups include, for example, monocyclic or polycyclic groups containing only nitrogen atoms as a hetero atom or containing a sulfur atom or oxygen atom in addition to the nitrogen atom. For example, there may be cited heterocyclic groups such as pyrrolyl, pyridyl and its N-oxide, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl, benzoxazolyl and the like. These groups may have as a substitutent a lower alkyl group such as methyl, ethyl, propyl and the like, an amino group, a dialkylaminoalkyl group such as dimethylaminoethyl, dimethylaminomethyl, diethylaminoethyl and the like, or a carboxyalkyl group such as carboxymethyl, carboxyethyl, and the like.

Examples of the pharmaceutically acceptable salts of the compounds of the formula (I) are alkali metal salts such as sodium salts, potassium salts, ammonium salts, triethylamine salts, dicyclohexylamine salts, procaine salts, and the like.

The compounds of this invention can be synthesized by the following process.

The compounds of this invention represented by the formula:

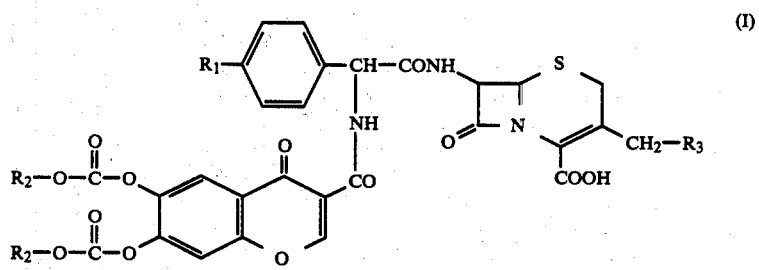

wherein $R_1$ represents a hydrogen atom or a hydroxyl group, $R_2$ represents a lower alkyl group or a chloro-substituted lower alkyl group, and $R_3$ represents a lower alkanoyloxy group or a nitrogen-containing heterocyclic thio group,
can be obtained by reacting a compound expressed by the formula:

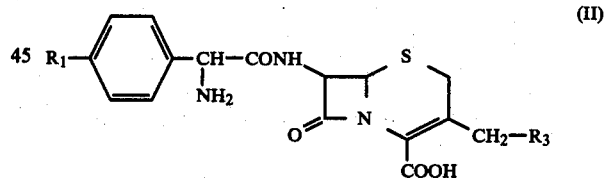

wherein $R_1$ and $R_3$ are as defined above, or its salt with a compound of the formula:

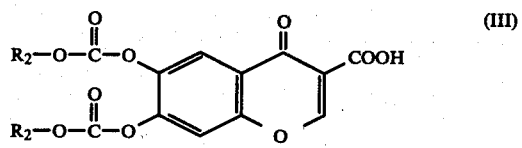

wherein $R_2$ is as defined above, or its reactive derivative. If desired, the compounds of the formula (I) are converted to their salts in a conventional manner.

When a compound of the formula (III) which is a carboxylic acid (-COOH) is used in the above reaction, the reaction is carried out preferably in the presence of a condensing agent such as N,N'-dicyclohexylcarbodiimide, N,N'-diethylcarbodiimide, N-cyclohexyl-N'-morpholinoethylcarbodiimide, a trialkyl phosphite, ethyl polyphosphate, phosphorus oxychloride, oxalyl chloride, and the like. The reactive derivative of the compound of the formula (III) used in the above reaction may be an acid halide such as an acid chloride, bromide and the like, a symmetric acid anhydride, a mixed acid anhydride with a carboxylic acid such as a chloroformic ester, trimethylacetic acid, thioacetic acid, diphenylacetic acid and the like, an active ester with 2-mercaptopyridine, cyanomethanol, p-nitrophenol, 2,4-dinitrophenol, pentachlorophenol, and the like, and an active acid amide such as an N-acylsaccharin, N-acyl phthalimide, and the like.

The above N-acylation reaction may be carried out at a temperature of $-50°$ C. to 50° C., preferably $-20°$ C. to 30° C., in an inert solvent in the presence or absence of a basic reagent or a silylating agent. Examples of the inert solvent are acetone, tetrahydrofuran, dimethyl acetamide, dimethyl formamide, dioxane, dichloromethane, chloroform, benzene, toluene, ethyl acetate, and mixtures thereof.

Examples of the basic reagents include alkali hydroxides such as sodium hydroxide, potassium hydroxide and the like, alkali hydrogen carbonates such as potassium hydrogen carbonate, sodium hydrogen carbonate and the like, and amines such as triethylamine, pyridine, dimethylaniline, N-methylmorpholine and the like.

As the silylating agent, there may be cited, for example, N,O-bis(trimethylsilyl)acetamide, hexamethyldisilazane, N-trimethylsilylacetamide, and the like.

The compound of the formula (II), a starting compound in the present synthesizing process, may be produced by methods which are shown, for example, in Belgian Pat. No. 635,137, British Pat. No. 1,240,687, or The Journal of Antibiotics, Vol. 29, page 65 (1976).

The compound of the formula (III) and its reactive derivative (acid halide) as the other starting compound may be produced by the following process.

(1) A compound represented by the formula:

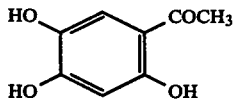

(IV)

is reacted with a chloroformic ester represented by the formula:

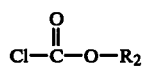

(V)

wherein $R_2$ is as defined hereinabove, to obtain a compound represented by the formula:

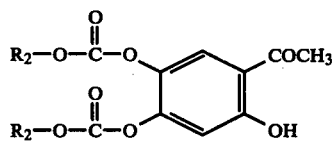

(VI)

wherein $R_2$ is as defined above.

(2) The compound of the formula (VI) is reacted with dimethyl formamide in the presence of an acid halide to obtain a compound of this invention represented by the formula:

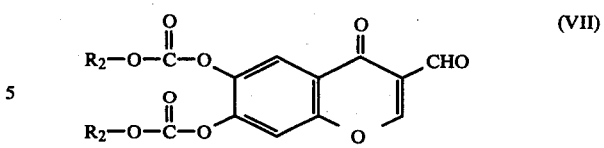

(VII)

wherein $R_2$ is as defined above.

(3) The compound of the formula (VII) is oxidized in the presence of an oxidizing agent to obtain a compound represented by the formula:

(III)

wherein $R_2$ is as defined above.

(4) A compound represented by the formula:

(VIII)

wherein $R_2$ is as defined above and X represents a halogen atom, can be obtained by reacting the compound of the formula (III) above with a halogenating agent.

In the above reaction, the reaction of the compound of the formula (IV) with the compound of the formula (V) in step (1) can be carried out in the presence of a base such as pyridine, triethylamine, N-methylmorpholine and the like at a temperature of preferably below room temperature.

The reaction of the compound of the formula (VI) with dimethyl formamide in step (2) can be carried out by using an inert solvent such as benzene, toluene, ethyl ether, tetrahydrofuran, dioxane and the like or an excessive amount of dimethyl formamide, the reactant, instead of the solvent. Examples of the acid halide are phosphorus oxychloride, thionyl chloride, phosgene, trichloromethyl chloroformate, phosphorus pentachloride, benzoyl chloride, p-toluenesulfonyl chloride, and the like.

Oxidation of the compound of the formula (VII) in step (3) is carried out using a chlorite-chlorine scavenger, a Jones reagent (chromic anhydride-sulfuric acid), sodium bichromate-sulfuric acid, and the like as an oxidizing agent.

Of the above oxidizing agents, the chlorite-chlorine scavenger system is most preferred in view of the yield of the product. Sodium chlorite and potassium chlorite may be cited as examples of the chlorite. The chlorine scavenger denotes a compound having the action of scavenging chlorine generated in the reaction system, and examples are sulfamic acid, resorcinol, pyroglutamic acid and the like. Sulfamic acid is most preferred. The oxidation reaction is carried out usually at $-10°$ to 40° C., preferably 10° to 20° C. Examples of the reaction solvent are non-hydrophilic solvents such as dichloromethane, chloroform, dichloroethane, ethyl acetate, benzene, toluene and the like, and hydrophilic solvents such as acetone dioxane, tetrahydrofuran, acetonitrile, and the like.

An ordinary halogenating agent may be used as the halogenating agent for the preparation of the compound of the formula (III) in step (4). For example, to obtain an acid chloride, phosphorus pentachloride, thionyl chloride, and the like may be cited.

The following compounds and their sodium salts may be cited as specific compounds of this invention.

7β-[D-2-[6,7-Bis(ethoxycarbonyloxy)chromone-3-carboxamide]-2-(4-hydroxyphenyl)acetamide]-3-[(1-carboxymethyl-5-tetrazolyl)-thiomethyl]-3-cephem-4-carboxylic acid, 7β-[D-2-[6,7-Bis(ethoxycarbonyloxy)chromone-3-carboxamide]-2-phenylacetamide]-3-[(1-carboxymethyl-5-tetrazolyl)thiomethyl]-3-cephem-4-carboxylic acid, 7β-[D-2-[6,7-Bis(ethoxycarbonyloxy)chromone-3-carboxamide]-2-(4-hydroxyphenylacetamide]-3-acetoxymethyl-3-cephem-4-carboxylic acid, 7β-[D-2-(6,7-Bis(ethoxycarbonyloxy)chromone-3-carboxamide]-2-phenylacetamide]-3-acetoxymethyl-3-cephem-4-carboxylic acid, 7β-[D-2-[6,7-Bis(2,2,2-trichloroethoxycarbonyloxy)-chromone-3-carboxamide]-2-(4-hydroxyphenyl)acetamide]-3-[(1-carboxymethyl-5-tetrazolyl)thiomethyl]-3-cephem-4-carboxylic acid, 7β-[D-2-[6,7-Bis(2,2,2-trichloroethoxycarbonyloxy)-chromone-3-carboxamide]-2-phenylacetamide]-3-[(1-carboxymethyl-5-tetrazolyl)thiomethyl]-3-cephem-4-carboxylic acid, 7β-[D-2-[6,7-Bis(2,2,2-trichloroethoxycarbonyloxy)-chromone-3-carboxamide]-2-(4-hydroxyphenyl)acetamide]-3-acetoxymethyl-3-cephem-4-carboxylic acid, 7β-[D-2-[6,7-Bis(2,2,2-trichloroethoxycarbonyloxy)-chromone-3-carboxamide]-2-phenylacetamide]-3-acetoxymethyl-3-cephem-4-carboxylic acid, 7β-[D-2-[6,7-Bis(ethoxycarbonyloxy)chromone-3-carboxamide]-2-(4-hydroxyphenyl)acetamide]-3-[(1-methyl-5-tetrazolyl)thiomethyl]-3-cephem-4-carboxylic acid, and 7β-[D-2-[6,7-Bis(ethoxycarbonyloxy)chromone-3-carboxamide]-2-(4-hydroxyphenyl)acetamide]-3-[(5-methyl-2-(1,3,4-thiadiazolyl)-thiomethyl]-3-cephem-4-carboxylic acid.

The compounds of this invention exhibit excellent antibacterial activity, and are effective against Gram-positive and Gram-negative bacteria. They are especially effective clinically against bacteria causing vicious infections, such as *Pseud. aeruginosa, Ser. marcescens* and *Proteus morganii,* and the like.

The compounds of this invention have low toxicity. For example, the acute toxicity values [$LD_{50}$ (mice, oral)] of 7β-[D-2-[6,7-bis(ethoxycarbonyloxy)chromone-3-carboxamide]-2-(4-hydroxyphenyl)acetamide]-3-[(1-carboxymethyl-5-tetrazolyl)]-3-cephem-4-carboxylic acid and 7β-[D-2-[6,7-bis(ethoxycarbonyloxy)-chromone-3-carboxamide]-2-(4-hydroxyphenyl)acetamide]-3-cephem-4-carboxylic acid are both more than 5 g/kg.

The dose of the compound of this invention as an antibacterial agent is generally 2 to 300 mg/kg/day, preferably 10 to 100 mg/kg/day. The present drug is administered orally in the form of a powder, granules, tablets, capsules, syrup, and the like or parenterally in the form of an injectable preparation, a suppository, and the like. These pharmaceutical preparations can be produced in a conventional manner using pharmaceutically acceptable carriers.

The following Examples and Experimental Examples illustrate the present invention in detail.

EXPERIMENTAL EXAMPLE 1

6,7-Bis(ethoxycarbonyloxy)chromone-3-carboxaldehyde (intermediate)

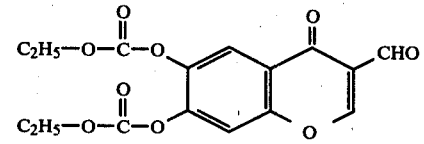

(a) 4,5-Bis(ethoxycarbonyloxy)-2-hydroxyacetophenone 2,4,5-Trihydroxyacetophenone (3.36 g) was dissolved in 150 ml of ethyl acetate, and 3.24 ml of pyridine was added at about $-5°$ C. with stirring. Then, 50 ml of a solution of 3.8 ml of ethyl chloroformate in ethyl acetate was added dropwise over 30 minutes. The mixture was stirred for 10 minutes at the same temperature. The resulting precipitate was collected by filtration and washed three times with 10 ml of ethyl acetate. The washings and the filtrate were combined, and the mixture was washed with water (once) and a saturated aqueous solution of sodium chloride (three times) and dried over magnesium sulfate. The solvent was distilled off, and the residue was recrystallized from ethyl ether-ethanol. The crystals were collected by filtration, and washed with ethanol and n-hexane and dried to afford 4.60 g of the desired product.

Melting point: 58°–60° C.

(b) 6,7-Bis(ethoxycarbonyloxy)chromone-3-carboxaldehyde

The above compound (a) (37.47 g) was dissolved in 300 ml of dimethyl formamide. The solution was cooled to about $-5°$ C., and with stirring, 120 ml of phosphorus oxychloride was added dropwise over 40 minutes. The mixture was stirred at room temperature for 5.5 hours. The reaction mixture was added to 3 liters of ice water, and stirred for 20 minutes. The resulting precipitate was collected by filtration, washed with water, and dissolved in ethyl acetate. The ethyl acetate solution was washed with water three times and dried over magnesium sulfate. The solvent was distilled off, and ethanol was added to the residue to solidify it. The solidified product was collected by filtration, washed with ethanol and n-hexane, and then dried to afford 28.5 g of the desired product.

Melting point: 101°–102° C.

Mass spectrum (m/e): 350 (M+)

Elemental analysis for $C_{16}H_{14}O_9$:

|  | C | H |
|---|---|---|
| Calculated (%): | 54.86 | 4.03 |
| Found (%): | 54.70 | 3.81 |

Infrared absorption spectrum (cm$^{-1}$, nujol): 1775, 1765, 1700, 1660, 1625.

NMR spectrum (δ, CDCl$_3$):
1.45 (6H, t, J=7 Hz), 4.40 (4H, q, J=7 Hz),
7.62 (1H, s), 8.17 (1H, s),
8.53 (1H, s), 10.33 (1H, s).

EXPERIMENTAL EXAMPLE 2

6,7-Bis(ethoxycarbonyloxy)chromone-3-carboxylic acid (intermediate)

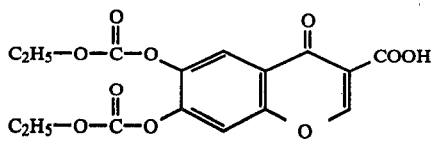

The compound (1.05 g) obtained in (b) of Experimental Example 1 was dissolved in 31.5 ml of dichloromethane, and a solution of 1.05 g of sulfamic acid in 18.9 ml of water was added at 10° C. with stirring. Then, a solution of 525.6 mg of sodium chlorite in 1.2 ml of water was added. The solution was stirred at the same temperature for 1 hour, and allowed to separate. The dichloromethane layer was washed with water (once) and then with a saturated aqueous solution of sodium chloride (twice), and dried over magnesium sulfate. The solvent was distilled off, and ethyl ether was added to the residue to solidify it. The solidified product was collected by filtration, and dried to afford 950 mg of the desired product.

Melting point: 107°–109° C.
Mass spectrum (m/e): 366 (M+)
Elemental analysis for $C_{16}H_{14}O_{10}$:

|  | C | H |
| --- | --- | --- |
| Calculated (%): | 52.47 | 3.85 |
| Found (%): | 52.57 | 3.63 |

Infrared absorption spectrum (cm$^{-1}$, nujol): 1765, 1625.
NMR spectrum (δ, CDCl$_3$):
1.38 (6H, t, J=7 Hz), 4.37 (4H, q, J=7 Hz),
7.74 (1H, s), 8.21 (1H, s),
8.98 (1H, s).

EXPERIMENTAL EXAMPLE 3

6,7-Bis(ethoxycarbonyloxy)chromone-3-carbonyl chloride (intermediate)

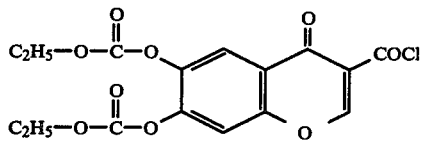

The compound (1.1 g) of Experimental Example 2 was dissolved in 20 ml of benzene, and 2 ml of thionyl chloride was added dropwise at room temperature with stirring. Then, the mixture was refluxed with stirring. The reaction mixture was concentrated, and n-hexane was added to the concentrate to crystallize it. The resulting crystals were collected by filtration, washed with n-hexane and dried to afford 980 mg of the desired product.

Melting point: 89°–92° C.
Mass spectrum (m/e): 384 (M+), 386 (M+).
Infrared absorption spectrum (cm$^{-1}$, nujol): 1770, 1680, 1620, 1565.

EXPERIMENTAL EXAMPLE 4

6,7-Bis(2,2,2-trichloroethoxycarbonyloxy)chromone-3-carboxaldehyde (intermediate)

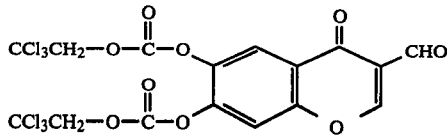

(a) 2-Hydroxy-4,5-bis(2,2,2-trichloroethoxycarbonyloxy)acetophenone 2,4,5-Trihydroxyacetophenone (16.8 g) was dissolved in 500 ml of ethyl acetate, and 15.98 ml of pyridine was added at about −5° C. with stirring. Then, a solution of 26.82 ml of 2,2,2-trichloroethyl chloroformate in 70 ml of ethyl acetate was added dropwise over the course of 2.5 hours. The mixture was stirred at the same temperature for 15 minutes. The precipitate formed was collected by filtration and washed with ethyl acetate. The washing and the filtrate were combined, and the mixture was washed with water (once) and a saturated aqueous solution of sodium chloride (twice), and dried over magnesium sulfate. The solvent was distilled off, and the residue was recrystallized from ethyl ether-ethanol. The crystals were collected by filtration, washed with ethanol and n-hexane and dried to afford 43.6 g of the desired product.

Melting point: 107.5°–108° C.

(b) 6,7-Bis(2,2,2-trichloroethoxycarbonyloxy)chromone-3-carboxaldehyde

The compound (25.95 g) obtained in (a) above was dissolved in 125 ml of dimethyl formamide. The solution was cooled to about −5° C., and with stirring, 50 ml of phosphorus oxychloride was added dropwise over 1 hour. The mixture was stirred at room temperature for 5.5 hours. The reaction mixture was added to 1.5 liters of ice water, and stirred for 20 minutes. The precipitate formed was collected by filtration, and washed with water. The product was dissolved in ethyl acetate, washed with water and dried over magnesium sulfate. The solvent was distilled off, and ethanol was added to the residue to solidify it. The solidified product was collected by filtration, washed with ethanol and then with n-hexane, and dried to afford 18.5 g of the desired product.

Melting point: 153°–155° C.
Mass spectrum (m/e): 554 (M+), 556 (M+), 558 (M+), 560 (M+).
Elemental analysis for $C_{10}H_8Cl_6O_9$:

|  | C | H |
| --- | --- | --- |
| Calculated (%): | 34.51 | 1.45 |
| Found (%): | 34.63 | 1.47 |

Infrared absorption spectrum (cm$^{-1}$, nujol): 1780, 1720, 1693, 1660, 1626, 1566.
NMR spectrum (δ, CDCl$_3$):
4.92 (4H, s), 7.68 (1H, s),
8.27 (1H, s), 8.55 (1H, s),
10.36 (1H, s).

EXPERIMENTAL EXAMPLE 5

6,7-Bis(2,2,2-trichloroethoxycarbonyloxy)chromone-3-carboxylic acid (intermediate)

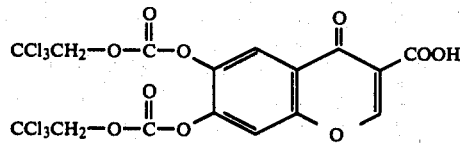

The compound (838.4 mg) obtained in Experimental Example 4, (b) was dissolved in 16 ml of dichloromethane, and with stirring at 10° C., a solution of 525 mg of sulfamic acid in 9.5 ml of water was added, followed by addition of a solution of 262.8 mg of sodium chlorite in 0.6 ml of water. The mixture was stirred for 1 hour at the same temperature. The reaction mixture was allowed to separate. The dichloromethane layer was washed with water and then with a saturated aqueous solution of sodium chloride, and then dried over magnesium sulfate. The solvent was distilled off, and the residue was recrystallized from ethyl ether to afford 685 mg of the desired product.

Melting point: 166°–167° C.

Mass spectrum (m/e): 570 (M+), 572 (M+), 574 (M+), 576 (M+)

Elemental analysis for $C_{16}H_8Cl_6O_{10}$:

|  | C | H |
|---|---|---|
| Calculated (%): | 33.54 | 1.41 |
| Found (%): | 33.46 | 1.35 |

Infrared absorption spectrum (cm$^{-1}$, nujol): 1780, 1620, 1590, 1570.

NMR spectrum (δ, CDCl$_3$):
4.92 (4H, s), 7.80 (1H, s),
8.31 (1H, s), 9.02 (1H, s),
12.97 (1H, br. s).

EXPERIMENTAL EXAMPLE 6

6,7-Bis(2,2,2-trichloroethoxycarbonyloxy)chromone-3-carbonyl chloride (intermediate)

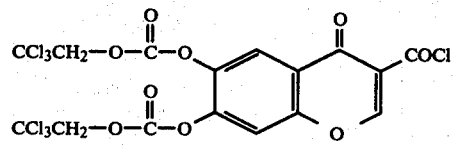

The compound (57.3 mg) obtained in Experimental Example 5 was dissolved in 10 ml of benzene, and with stirring at room temperature, 0.5 ml of thionyl chloride was added. The mixture was refluxed for 3 hours with stirring. The reaction mixture was concentrated, and 5 ml of n-hexane was added to the concentrate to crystallize it. The resulting crystals were collected by filtration, washed with n-hexane and dried to afford 34.8 mg of the desired product.

Melting point: 140° to 142° C.

Mass spectrum (m/e): 590 (M+), 592 (M+), 594 (M+), 596 (M+).

Infrared absorption spectrum (cm$^{-1}$, nujol): 1765, 1655, 1620, 1565.

EXAMPLE 1

7β-[D-2-[6,7-Bis(ethoxycarbonyloxy)chromone-3-carboxamide]-2-(4-hydroxyphenyl)acetamide]-3-[(1-carboxymethyl-5-tetrazolyl)thiomethyl]-3-cephem-4-carboxylic acid

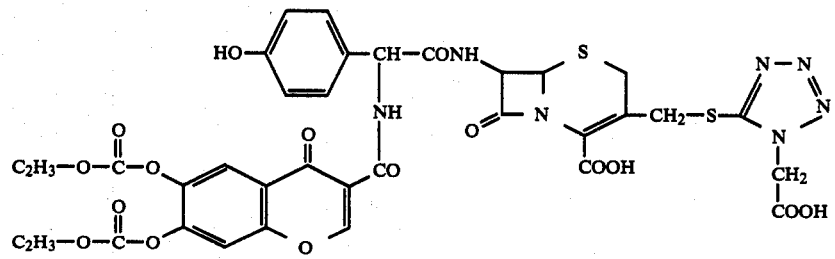

7β-[D-2-Amino-2-(4-hydroxyphenyl)acetamide]-3-[(1-carboxymethyl-5-tetrazolyl)thiomethyl]-3-cephem-4-carboxylic acid.trifluroacetic acid salt (0.318 g) was suspended in 5 ml of tetrahydrofuran. To the suspension was added 0.56 ml of N,O-bis(trimethylsilyl)acetamide at 0° C. with stirring. The mixture was stirred at the same temperature for 30 minutes. The acid chloride (192 mg) obtained in Experimental Example 3 was dissolved in 2 ml of tetrahydrofuran, and the solution was added. The mixture was stirred at 0° C. for 1 hour. The reaction mixture was concentrated to about 5 ml. The concentrate was added to 75 ml of 0.25 N hydrochloric acid cooled with ice. The precipitate formed was collected by filtration, washed with water and dried to afford 0.431 g of the desired product.

Melting point: 158°–163° C. (decomp.)

Elemental analysis for $C_{35}H_{31}N_7O_{16}S_2$:

|  | C | H | N |
|---|---|---|---|
| Calculated (%): | 48.33 | 3.59 | 11.27 |
| Found (%): | 47.71 | 3.79 | 10.58 |

Infrared absorption spectrum (cm$^{-1}$, nujol): 1770, 1660, 1610.

NMR spectrum (δ, DMSO-d$_6$):
1.31 (6H, t, J=7 Hz), 3.52 (1H, d, J=18 Hz),
3.64 (1H, d, J=18 Hz), 4.08–4.56 (6H, m),
4.97 (1H, d, J=4.5 Hz), 5.28 (2H, s),
5.60–5.82 (2H, m), 6.71 (2H, d, J=8 Hz), 7.25 (2H, d, J=8 Hz), 8.02 (1H, s),
8.18 (1H, s), 9.02 (1H, s),
9.36 (1H, d, J=8 Hz), 9.95 (1H, d, J=8 Hz).

Antibacterial activity (MIC, μg/ml):

| | |
|---|---|
| *Staph. aureus* 209-P | 6.25 |
| *Escher. coli* NIHJ | 0.4 |
| *Kleb. pneumoniae* EK-6 | ≦0.05 |

| | |
|---|---|
| Proteus morganii EP-14 | 1.56 |
| Pseud. aeruginosa EP172 | 0.8 |
| Ser. marcescens ES-75 | ≦0.05 |

EXAMPLE 2

7β-[D-2-[6,7-Bis(2,2,2-trichloroethoxycarbonyloxy)-chromone-3-carboxamide]-2-(4-hydroxyphenyl)acetamide]-3-[(1-carboxymethyl-5-tetrazolyl)thiomethyl]-3-cephem-4-carboxylic acid.

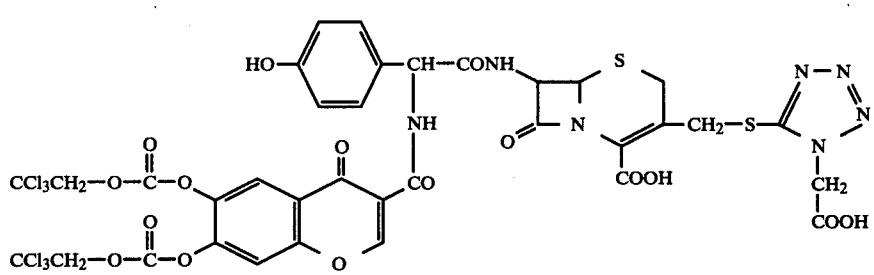

7β-[D-2-Amino-2-(4-hydroxyphenyl)acetamide]-3-[(1-carboxymethyl-5-tetrazolyl)thiomethyl]-3-cephem-4-carboxylic acid.trifluoroacetic acid salt (0.318 g) was suspended in 10 ml of tetrahydrofuran. To the suspension was added 0.62 ml of N,O-bis(trimethylsilyl)acetamide at 0° C. with stirring, and the mixture was stirred at the same temperature for 30 minutes. A solution of 296 mg of the acid chloride obtained in Experimental Example 6 in 2 ml of tetrahydrofuran was added, and the mixture was stirred at 0° C. for 1 hour. The reaction mixture was added to 70 ml of 0.5 N hydrochloric acid cooled with ice. The resulting precipitate was collected by filtration, washed with ice water, and dried to afford 0.528 g of the desired product.

Melting point: 170°–175° C. (decomp.)

Elemental analysis for $C_{35}H_{25}Cl_6N_7O_{16}S_2$:

| | C | H | N |
|---|---|---|---|
| Calculated (%): | 39.05 | 2.34 | 9.11 |
| Found (%): | 39.25 | 2.68 | 8.12 |

Infrared absorption spectrum ($cm^{-1}$, nujol): 1780, 1670, 1615.

NMR spectrum (δ, DMSO-$d_6$):
3.54 (1H, d, J=18 Hz), 3.66 (1H, d, J=18 Hz),
4.21 (1H, d, J=14 Hz), 4.42 (1H, d, J=14 Hz),
4.99 (1H, d, J=5 Hz), 5.09 (2H, s),
5.11 (2H, s), 5.28 (2H, s),
5.60–5.86 (2H, m), 6.72 (2H, d, J=8 Hz),
7.26 (2H, d, J=8 Hz), 8.16 (1H, s),
8.32 (1H, s), 9.05 (1H, s),
9.40 (1H, d, J=8 Hz), 9.94 (1H, d, J=8 Hz)

Antibacterial activity (MIC, μg/ml):

| | |
|---|---|
| Staph. aureus 209-P | 12.5 |
| Escher. coli NIHJ | 1.56 |
| Kleb. pneumoniae EK-6 | ≦0.05 |
| Proteus morganii EP-14 | 3.13 |
| Pseud. aeruginosa EP-172 | 1.56 |
| Ser. marcescens ES-75 | 0.1 |

EXAMPLE 3

7β-[D-2-[6,7-Bis(ethoxycarbonyloxy)chromone-3-carboxamide]-2-phenylacetamide]-3-acetoxymethyl-3-cephem-4-carboxylic acid

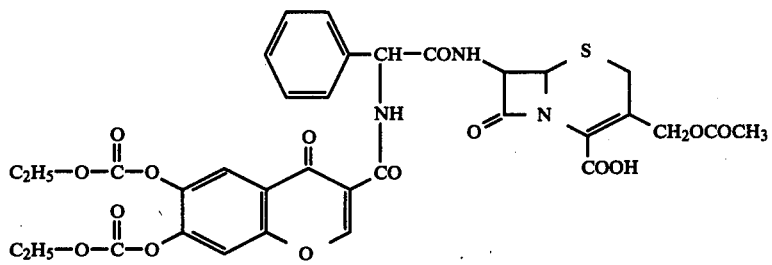

Cephaloglycine (0.405 g) was suspended in 10 ml of ethyl acetate, and to the suspension was added 0.50 ml of N,O-bis(trimethylsilyl)acetamide at 0° C. with stirring. The mixture was stirred at room temperature for 1 hour. A suspension of 0.385 g of the acid chloride of Experimental Example 3 in ethyl acetate was added to the resulting solution at 0° C. with stirring, and the mixture was stirred at the same temperature for 1 hour. The solvent was distilled off, and the residue was dissolved in 5 ml of acetone. The solution was added dropwise to 70 ml of 0.25 N hydrochloric acid at 0° C. with stirring. The resulting precipitate was collected by filtration, washed with water, and then dried to afford 0.654 g of a crude product. The crude product was washed with ethyl ether, and dried to afford 0.600 g of the desired product.

Melting point: 142°–145° C. (decomp.)

Elemental analysis for $C_{34}H_{31}N_3O_{15}S$:

| | C | H | N |
|---|---|---|---|
| Calculated (%): | 54.18 | 4.15 | 5.58 |
| Found (%): | 52.99 | 3.96 | 5.76 |

Infrared absorption spectrum ($cm^{-1}$, nujol): 1770, 1735, 1665, 1620

NMR spectrum (δ, DMSO-$d_6$):

1.30 (6H, t, J=7 Hz), 2.00 (3H, s),
3.38 (1H, d, J=18 Hz), 3.48 (1H, d, J=18 Hz),
4.26 (4H, q, J=7 Hz), 4.64 (1H, d, J=14 Hz),
4.90 (1H, d, J=14 Hz), 4.98 (1H, d, J=5 Hz),
5.56–5.92 (2H, m), 7.20–7.54 (5H, m),
7.96 (1H, s), 8.14 (1H, s),
8.98 (1H, s), 9.44 (1H, d, J=8 Hz),
10.04 (1H, d, J=8 Hz)

Antibacterial activity (MIC, μg/ml)

| Staph. aureus 209-P | 0.4 |
| Escher. coli NIHJ | 3.13 |
| Kleb. pneumoniae EK-6 | ≦0.05 |
| Proteus morganii EP-14 | 12.5 |
| Pseud. aeruginosa EP-172 | 1.56 |
| Ser. marcescens ES-75 | 0.2 |

EXAMPLE 4

7β-[D-2-[6,7-Bis(ethoxycarbonyloxy)chromone-3-carboxamide]-2-(4-hydroxyphenyl)acetamide]-3-acetoxymethyl-3-cephem-4-carboxylic acid

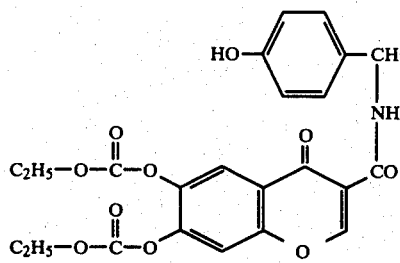

7β-[D-2-Amino-2-(4-hydroxyphenyl)acetamide]-3-acetoxymethyl-3-cephem-4-carboxylic acid (1.0 g) was suspended in 30 ml of tetrahydrofuran, and with stirring, 2.0 ml of N,O-bis(trimethylsilyl)acetamide was added dropwise. The mixture was further stirred to form a solution. To the resulting solution was added a solution of 912 mg of the acid chloride of Experimental Example 3 in 5 ml of tetrahydrofuran under ice cooling. The mixture was stirred for 1 hour under ice cooling and then for 1 hour at room temperature. The reaction mixture was concentrated to 5 ml, and the concentrate was added dropwise to 20 ml of 0.5 N hydrochloric acid with stirring. The resulting precipitate was collected by filtration, washed with water, and then dissolved in ethyl acetate. The solution was washed with water three times, and dried over magnesium sulfate. The solvent was distilled off, and the residue was dissolved in 5 ml of ethyl acetate. The solution was added dropwise to 50 ml of ethyl ether with stirring. The resulting precipitate was collected by filtration, washed with ethyl ether and dried to afford 550 mg of the desired product.

Melting point: 213°–215° C. (decomp.)

Infrared absorption spectrum (cm$^{-1}$, nujol): 1785, 1770, 1735, 1680, 1660, 1620.

NMR spectrum (δ, DMSO-d$_6$):
1.31 (6H, t, J=7 Hz), 2.02 (3H, s),
3.3–3.6 (3H, b s), 4.31 (2H, q, J=7 Hz),
4.32 (2H, q, J=7 Hz), 4.65 (1H, d, J=14 Hz),
4.99 (1H, d, J=14 Hz), 5.03 (1H, d, J=4.5 Hz),
5.6–5.9 (2H, m), 6.72 (2H, d, J=8 Hz),
7.26 (2H, d, J=8 Hz), 8.04 (1H, s),
8.19 (1H, s), 9.36 (1H, d, J=8 Hz),
9.96 (1H, d, J=8 Hz).

What is claimed is:

1. A cephem derivative represented by the formula:

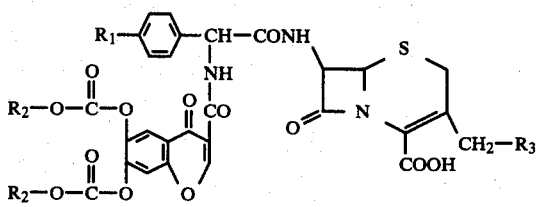
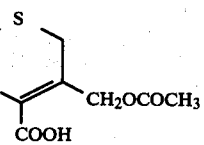

wherein $R_1$ represents hydrogen or hydroxyl, $R_2$ represents lower alkyl or chloro-substituted lower alkyl, and $R_3$ represents lower alkanoyloxy or carboxyalkyl substituted tetrazolyl-thio or a pharmaceutically acceptable salt thereof.

2. A compound as claimed in claim 1 wherein $R_3$ is acetoxy or (1-carboxymethyl-5-tetrazolyl)-thio.

3. A compound as claimed in claim 2 which is 7β-[D-2-[6,7-bis(ethoxycarbonyloxy)chromone-3-carboxamide]-2-(4-hydroxyphenyl)acetamide]-3-[(1-carboxymethyl-5-tetrazolyl)thiomethyl]-3-cephem-4-carboxylic acid or the sodium salt thereof.

4. A compound as claimed in claim 2 which is 7β-[D-2-[6,7-bis(ethoxycarbonyloxy)chromone-3-carboxamide]-2-(4-hydroxyphenyl)acetamide]-3-acetoxymethyl-3-cephem-4-carboxylic acid or the sodium salt thereof.

5. An antibacterial pharmaceutical preparation which contains a therapeutically effective amount of a compound as claimed in claim 1 and a pharmaceutically acceptable carrier.

* * * * *